US008914123B2

(12) United States Patent
Rigaux

(10) Patent No.: US 8,914,123 B2
(45) Date of Patent: Dec. 16, 2014

(54) APPARATUS FOR ELECTRO-INHIBITION OF FACIAL MUSCLES

(75) Inventor: Pierre Rigaux, Liège (BE)

(73) Assignee: Cefaly Technology SPRL, Herstal (BE)

( * ) Notice: Subject to any disclaimer, the term of this patent is extended or adjusted under 35 U.S.C. 154(b) by 571 days.

(21) Appl. No.: 11/667,223

(22) PCT Filed: Sep. 7, 2005

(86) PCT No.: PCT/BE2005/000135
§ 371 (c)(1),
(2), (4) Date: May 7, 2007

(87) PCT Pub. No.: WO2006/063417
PCT Pub. Date: Jun. 22, 2006

(65) Prior Publication Data
US 2007/0276451 A1 Nov. 29, 2007

(30) Foreign Application Priority Data

Dec. 14, 2004 (EP) .................................. 04447276

(51) Int. Cl.
*A61N 1/36* (2006.01)
*A61N 1/04* (2006.01)
*A61N 1/32* (2006.01)

(52) U.S. Cl.
CPC ............ *A61N 1/0452* (2013.01); *A61N 1/0456* (2013.01); *A61N 1/0472* (2013.01); *A61N 1/328* (2013.01); *A61N 1/0492* (2013.01); *A61N 1/32* (2013.01)
USPC .............. 607/48; 600/382; 600/386; 607/139

(58) Field of Classification Search
USPC ............. 607/66–76, 135, 139, 141, 149, 140, 607/152, 153; 600/391, 382–384; 601/71; 604/20
See application file for complete search history.

(56) References Cited

U.S. PATENT DOCUMENTS 2,782,786 A * 2/1957 Krasno ........................ 600/384
3,620,219 A * 11/1971 Barker ......................... 607/139

(Continued)

FOREIGN PATENT DOCUMENTS

WO WO 00/71075 11/2000
WO WO 01/03638 1/2001

OTHER PUBLICATIONS

International Search Report, International Application No. PCT/BE2005/000135, date of actual completion of the international search Jan. 10, 2006, date of actual mailing of the international search report Jan. 17, 2006, 4 pages, European Patent Office.

(Continued)

*Primary Examiner* — Kennedy Schaetzle
*Assistant Examiner* — Erica Lee
(74) *Attorney, Agent, or Firm* — Reinhart Boerner Van Deuren P.C.

(57) ABSTRACT

The invention concerns a method for performing an electric inhibition of the facial muscles for purely aesthetic purposes, using a device comprising a support at the head of a user (1), two contact electrodes (2), an electronic circuit (3) for generating low-voltage electric pulses at said electrodes (2), a direct current electric power supply (4) and means for fixing and locking (7) said components on the head. The invention is characterized in that it includes the following steps: placing the electrodes (2) on either side of the upper part of the nose, at the glabella; passing the electric pulses via the electrodes (2) through the pyramidal muscle of the nose so as to cause said pyramidal muscle of the nose to relax and hence its antagonist muscle, the forehead muscle and the double eyebrow muscle.

16 Claims, 4 Drawing Sheets

(56) References Cited

U.S. PATENT DOCUMENTS

| | | | |
|---|---|---|---|
| 3,709,228 A | 1/1973 | Barker | |
| 3,971,387 A * | 7/1976 | Mantell | 607/140 |
| 4,165,750 A * | 8/1979 | Aleev et al. | 607/48 |
| 4,209,234 A * | 6/1980 | McCooeye | 351/62 |
| 4,288,222 A * | 9/1981 | Kling | 434/272 |
| 4,841,954 A * | 6/1989 | Kalsi | 601/71 |
| 4,957,480 A | 9/1990 | Morenings | |
| 5,496,363 A | 3/1996 | Burgio et al. | |
| 5,527,357 A | 6/1996 | Springer, Jr. | |
| 5,726,916 A * | 3/1998 | Smyth | 702/151 |
| 5,785,040 A * | 7/1998 | Axelgaard | 600/391 |
| 5,913,836 A | 6/1999 | Groux | |
| 6,077,237 A * | 6/2000 | Campbell et al. | 600/587 |
| 6,198,955 B1 | 3/2001 | Axelgaard et al. | |
| 6,233,472 B1 * | 5/2001 | Bennett et al. | 600/383 |
| 6,654,626 B2 * | 11/2003 | Devlin et al. | 600/383 |
| 2002/0161416 A1 * | 10/2002 | Huang | 607/48 |
| 2003/0045922 A1 * | 3/2003 | Northrop | 607/139 |
| 2004/0073129 A1 * | 4/2004 | Caldwell et al. | 600/544 |
| 2004/0260359 A1 * | 12/2004 | Osrud | 607/48 |
| 2005/0038486 A1 * | 2/2005 | Mulholland | 607/48 |
| 2005/0187497 A1 * | 8/2005 | Nguyen | 601/21 |
| 2006/0077340 A1 * | 4/2006 | Curiel | 351/123 |
| 2006/0154078 A1 * | 7/2006 | Watanabe et al. | 428/413 |

OTHER PUBLICATIONS

D. A. Jones et al., "Excitation Frequency and Muscle Fatigue: Mechanical Responses during Voluntary and Stimulated Contractions", Experimental Neurology 64, pp. 401-413 (1979).

D. A. Jones, "Muscle Fatigue due to Changes Beyond the Neuromuscular Junction", Human Muscle Fatigue: Physiological Mechanisms, Pitman Medical London, 1981 (Ciba Foundation Symposium 82), pp. 178-196.

B. Bigland-Ritchie, "EMG and Fatigue of Human Voluntary and Stimulated Contractions", Human Muscle Fatigue: Physiological Mechanisms, Pitman Medical London 1981 (Ciba Foundation Symposium 82), pp. 130-156.

D. A. Jones, "High and Low-Frequency Fatigue Revisited", Acta Physiol. Scand. 156, 265-270 (1996).

J. B. Wal, "Modulation of Spasticity: Prolonged Suppression of a Spinal Reflex by Electrical Stimulation", Science 216: 203-204, 1982.

M. G. Levine et al., "Relaxation of Spasticity by Electrical Stimulation of Antagonist Muscles", Arch. Phys. Med. 33: 668-673, 1952.

\* cited by examiner

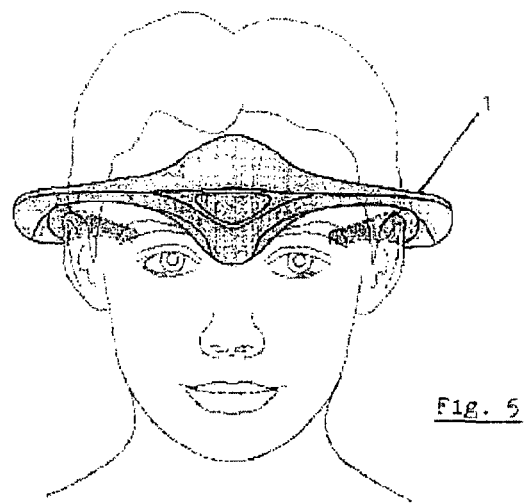
Fig. 5
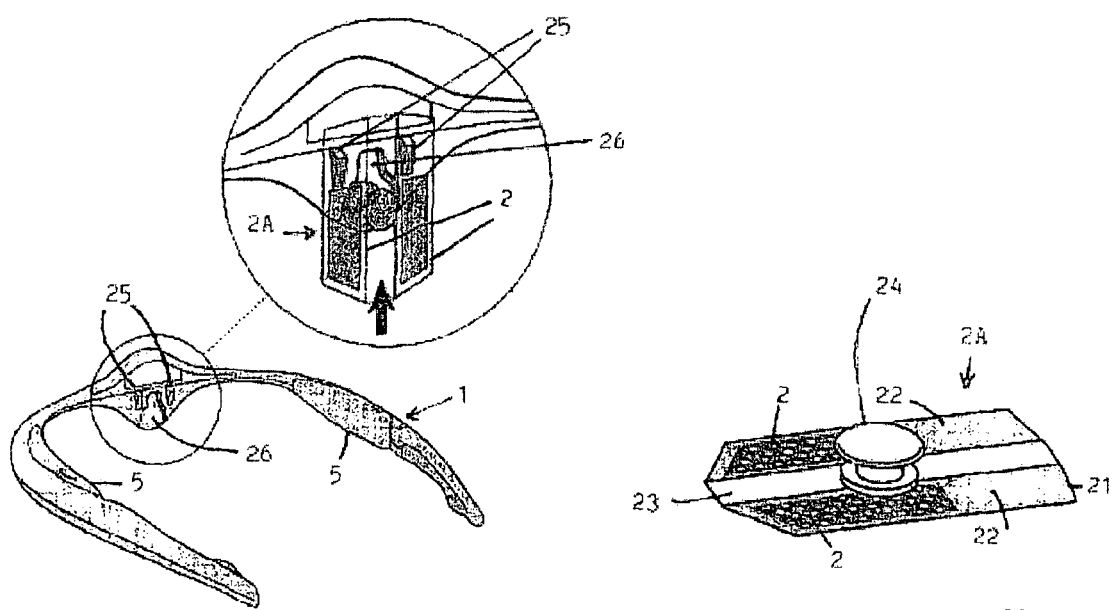
Fig. 6
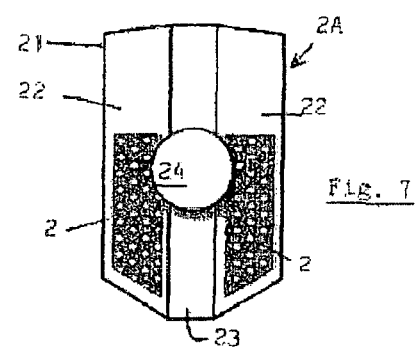
Fig. 7
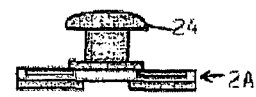

APPARATUS FOR ELECTRO-INHIBITION OF FACIAL MUSCLES

CROSS-REFERENCE TO RELATED PATENT APPLICATIONS

This patent application is the National Stage of International Application No. PCT/BE2005/000135 filed Sep. 7, 2005, that claims the benefit of European Application No. 04447276.9 filed Dec. 14, 2004.

FIELD OF THE INVENTION

The present invention relates to a device of electric inhibition or "electro-inhibition" that allows to relax specific muscles of the upper part of the face.

TECHNOLOGICAL BACKGROUND AND STATE OF THE ART

Wrinkles may be caused by a series of factors such as age, sun-induced damage, etc. but they are above all caused by facial expressions, i.e. repeated muscular contractions (expression of joy, anger, sadness, fear, surprise, etc.). They are therefore referred to as "expression wrinkles." These wrinkles, which mainly appear on the upper half of the face, are caused by the interactions between the skin and the underlying muscles. In particular, vertical wrinkles appear on the forehead, as wrinkles known as "crow's feet" at the eye corners, horizontal wrinkles on the forehead, etc.

Thus, wrinkles on the forehead, as well as most chronic cephaleae, commonly known as "headaches" or "migraines," are the result of prolonged tension that causes chronic contraction either of one of the three muscles of the upper part of the face: the forehead muscle (frontalis), the pair of muscles over the eyebrows (corrugators) and the pyramidal muscle of the nose (procerus), or even of several of them at the same time.

The pyramidal muscle is a fleshy little bundle of muscle located at the upper part of the back of the nose and between the eyes. It passes between the fascia covering the lower part of the nasal bone itself and the deep layer of skin in the area between the eyebrows. It draws the eyebrows downwards and towards the medial line, causing creases at the root of the nose. It is involved in frowning, the expression of concentration or simply to reduce dazzle in the case of bright light.

The forehead muscle is a flat muscle located under the skin of the forehead. It originates from the front edge of the epicranial aponeurosis and its fleshy fibres descend and attach to the deep layer of skin in the areas of the eyebrows and the area between the eyebrows. It raises the skin of the eyebrows and produces horizontal creases and wrinkles on the forehead.

Both eyebrow muscles pass on either sides of the glabella along the inner part of the superciliary arches. They originate from the inner edge of the superciliary arches and pass outwards along the arches to end in the deep layer of skin of the eyebrows. They draw the eyebrows towards the medial line and cause the vertical skin creases and wrinkles of the glabella.

Relaxing these muscles would therefore contribute to combat cephaleae and tension wrinkles. Moreover, relaxing these three muscles of the upper part of the face is likely to allow the activity of the muscles in the occipital zone to predominate. These muscles are the occipital muscle (occipitalis) and the two posterior auricular muscles (auricularis posterior).

This change of balance between facial muscles and occipital muscles in favour of the latter is likely to stretch the skin of the face, with the effect of a physiological facelift, which improves the appearance of the face.

Various treatments are already known in order to correct unsightly wrinkles such as wrinkles on the forehead or on the glabella, or crow's feet that appear on aging faces.

Some manufacturers of facial care creams recommend a suitable massage session to relax the facial muscles. However, one might doubt the effectiveness of such a treatment, above all if the expression wrinkles are already clearly marked.

There are also treatments for injecting products with a temporary action such as hyaluronic acid or type-A botulinic toxin, derived from the *Clostridium botulinum* bacterium (known by its commercial name Botox®). Botox® is injected at low doses into a specific muscle which becomes paralysed and therefore can no longer contract. These products have an active duration of a few months.

Permanent implants based on plastic microspheres or tubular implants made of PTFE, or alternatively collagen or silicone are also injected. The service life of these implants is several years. This relies on possibly reversible surgery.

However, these injection techniques entail a certain number of side effects such as the risk of developing an allergy or an oedema after injection, the risk of infection, red spots, bruises, irritations, etc.

Moreover, Botox® injections are in the patient's general circulation. One specific side effect is the undesirable paralysis observed in the muscles involved in swallowing (dysphagia).

In addition, muscular electro-stimulation is well known. Thus, for example, American U.S. Pat. No. 4,957,480 describes a method for toning the muscles and tissues of the face by stimulating the motor nerves and consequential contraction of the facial muscles, by applying galvanic currents of predetermined amplitude, frequency and polarity through electrodes moistened with a liquid solution of positively and negatively charged particles in order to insert it into the tissues so as to nurture the surrounding facial muscles and tissues. It is known from this document that it is possible, by this means, by the careful positioning of the electrodes directly on the muscle, to tire and consequently relax the forehead muscle, for example. The currents are between 300 and 640 µA with a frequency between 30 and 99 Hz, with alternating polarisation and an application time between 1 and 4 seconds, or even 10 seconds. The electric parameters used generate working fatigue similar to the muscle's voluntary fatigue, which produces only slight relaxation or none. This is the traditional field of electro-stimulation with frequencies lower than 100 Hz in order to produce short contractions.

American U.S. Pat. No. 3,709,228 describes a device for the electro-stimulation of the user's facial nerves and, consequently muscles, comprising a support resting on the nose and ears and having flexible arms that can extend in opposite directions and bear at their ends electrodes that contact the skin. A first electrode is positioned in order to stimulate the forehead branch of the facial nerve. A second electrode is positioned with a view to stimulate the maxillary branch of the facial nerve. Lastly, a third electrode is positioned with a view to stimulate the mandibular branch of the facial nerve. This document does not suggest the positioning of an electrode in the space between the eyebrows.

AIMS OF THE INVENTION

The present invention aims to provide a device that allows, by means of an electric current, to relax one or several muscles of the upper part of the face, in particular the forehead muscle (frontalis), both eyebrow muscles (corrugators) and the pyramidal muscle of the nose (procerus).

The invention aims in particular to propose a method for correcting wrinkles and relieving chronic cephaleae that is simple, non-invasive and devoid of side effects.

Main characteristic elements of the invention

A first object of the present invention, as stated in claim 1, relates to a method for the electro-inhibition of facial muscles for purely aesthetic purposes, using a device comprising a support on a user's head, two contact electrodes, an electronic circuit for generating low-voltage electric impulses at the level of said electrodes, a direct-current electricity supply and means for attaching and securing the above-mentioned elements on said head, characterised in the following steps:

arranging the electrodes on either sides of the upper part of the nose, at the level of the glabella;

passing said electric impulsions by the electrodes through the pyramidal muscle of the nose in order to relax said pyramidal muscle of the nose and consequently its antagonistic muscle, of the forehead muscle and the double eyebrow muscle.

A second object of the invention, relates to a device for the electro-inhibition of a facial muscles comprising a support at the level of a user's head, two contact electrodes to be located on either sides of the upper part of the nose, at the level of the glabella, an electronic circuit for generating low-voltage electric impulses at the level of said electrodes and a direct-current electricity supply, characterised in that both electrodes belong to a single electrode structure comprising a piece of cloth acting as support for both electrodes, the latter being covered on their inner face, i.e. the face that has to be in contact with the user's skin, by a self-adhesive conductive gel.

Lastly, a third aim of the invention, relates to a method of therapeutic treatment for tension cephaleae by means of the electric-inhibition of facial muscles using a device comprising a support on a user's head, two contact electrode, an electronic circuit for generating low-voltage electric impulses at the level of said electrodes, a direct-current electricity supply and means for attaching and securing the above-mentioned elements on said head, characterised in the following steps:

arranging the electrodes on either sides of the upper part of the nose, at the level of the glabella;

passing said electronic impulsions by the electrode through the pyramidal muscle of the nose in order to relax said pyramidal muscle of the nose and consequently its antagonistic muscle, of the forehead muscle and the double eyebrow muscle.

BRIEF DESCRIPTION OF THE FIGURES

FIG. 5 schematically shows a front view (without electrode) of the electro-inhibition device as in a second preferred embodiment of the present invention, placed on a user's head.

FIG. 6 shows a rear view of the device of FIG. 5 as well as a detailed view of the double electrode placed on its support.

FIG. 7 shows different views of the electrode of FIG. 6.

DESCRIPTION OF SEVERAL PREFERRED EMBODIMENTS OF THE INVENTION

Method

Figure 1:
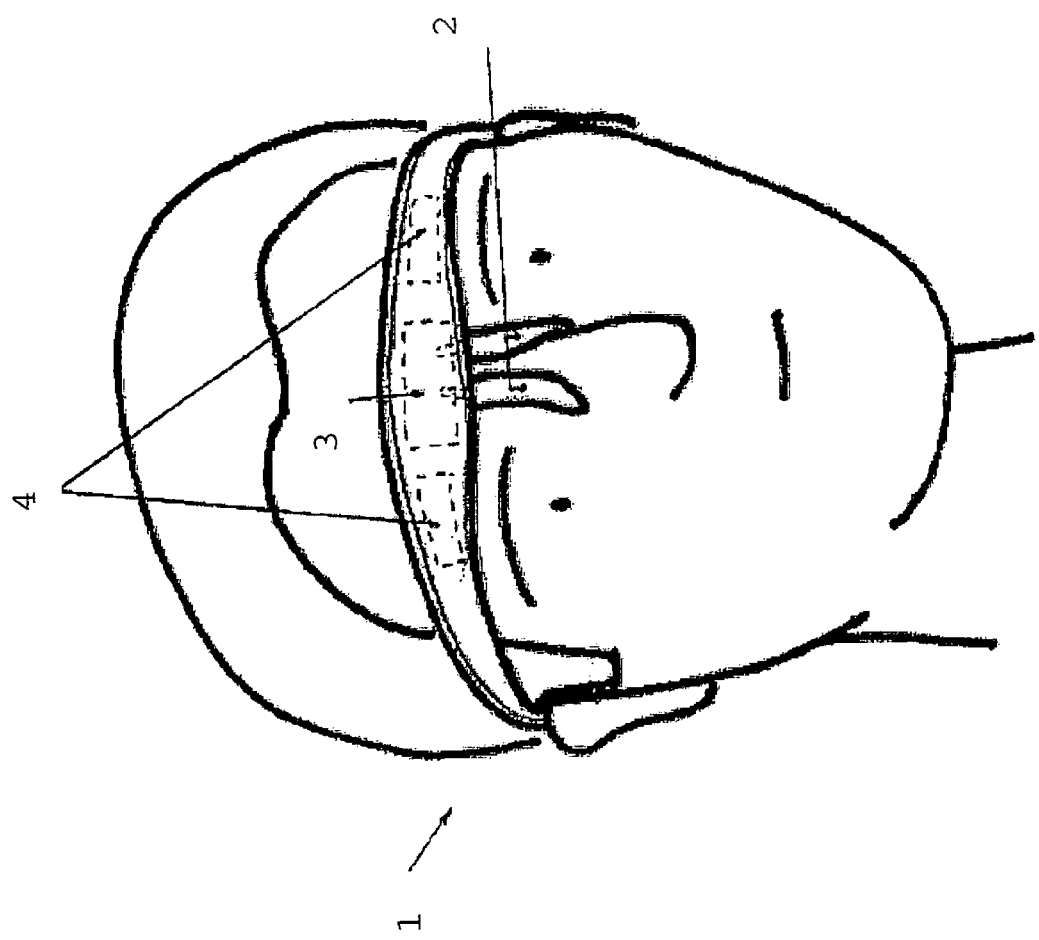
FIG. 1 schematically shows a front view of the electro-inhibition device as in a first preferred embodiment of the present invention, placed on a user's head.

The innovative principle on which the invention is based is to produce the inhibition of the three above-mentioned muscles in the upper part of the face by means of the application of an electric current to only one of these muscles, namely the pyramidal muscle. Thus, the specific positioning of the electrodes allows, by inhibiting the pyramidal muscle, reflex relaxation actions in the other muscles of the upper part of the face. This is therefore a method aimed at the reverse effect to that sought in electro-stimulation since the aim sought is the relaxation of the muscles and not their contraction.

Description of the Technique

According to the invention shown in FIG. 1 to 4, two small electrodes 2 are positioned parallel to each other in the space between the eyebrows known as the glabella, so that the inhibiting electric current passes through the pyramidal muscle of the nose. The electrodes 2 are supported by a headband 1.

These electrodes 2 have an essentially rectangular shape whose size is more or less 25 mm by 5 mm and are spaced apart by a distance of only 3 to 15 mm.

There is a double advantage to this particular positioning of the electrodes:

simplicity: with only two electrodes and a single stimulation channel, the relaxation effect is obtained on the three target muscles at the same time thanks to the physiological mechanisms described later (electric fatigue, inhibition and excitation reflexes of the tendon afferents), comfort: the very small gap between both electrodes (3 to 15 mm) allows to limit the uncomfortable sensations by reducing as much as possible the volume of tissues subjected to the electric current[1, 2]. In fact, this small gap between the electrodes has the double consequence that, for one thing, a very small surface area of skin is subjected to the electric current and that, for another, a very weak depth penetration of the current, the latter preferably circulating in the surface layers of the epidermis without exciting the very pain-sensitive nerve endings of the periosteum.

The current applied to the electrodes 2 consists of electric impulses that are known for being capable of triggering action potentials (APs) at the level of the motor nerves. These are rectangular impulses of a length between 30 and 100 μs and intensity between 0 and 30 mA[3]. The use of this type of impulses leads to an excitation of the pain fibres that is lower than that with the use of longer impulses. But any other type of impulse that is sufficient to trigger an AP in the motor neurons could be used.

An essential feature of the invention is that the current applied advantageously uses impulses with a frequency above 100 Hz, which causes very rapid electric fatigue of the pyramidal muscle[4, 5]. Thanks to this continuous excitation of the motor nerves, there occurs a rapid cessation of the electric activity of the muscle fibres innervated by the excited motor nerves[6]. With this impulse frequency maintained constant, the pyramidal muscle can no longer be excited within a few tens of seconds, loses its tone and thus relaxes completely[7].

The excitation of the motor neurons of the pyramidal muscle also causes the relaxation of its antagonistic muscle—the forehead muscle—via the reflex of reciprocal inhibition[8]. In fact, the electric impulses at the level of a muscle not only excite the motor neurons of this muscle but also the afferent proprioceptive fibres of this muscle. The excitation of the latter inhibits the motor neurons of the antagonistic muscle[9,10].

Moreover, the electrodes 2 being positioned at the level of the inner tendons of the eyebrow muscles, the current excites the afferent nerves of these tendons, i.e. those that leave the Golgi tendon spindle. Since these tendon afferents inhibit the motor neurons of their muscles, namely the double eyebrow muscle, their excitation by the electric impulses causes the relaxation of the muscle[11,12].

According to the invention, the electric frequencies are higher (at least 120 or 150 Hz) and the application time is much longer (typically more than 60 s) than in U.S. Pat. No. 4,957,480. This therefore does not lead to working fatigue but to an intense so-called "electric" fatigue[4,6]. The electric activity in the muscle fibre, characterised by rest and action potentials, disappears as a result of the accumulation of extracellular potassium ions ($K^+$). The electromechanical linkage of the muscular activity is broken by the disappearance of the electric potential of the fibres. This results in the total suspension of the mechanical activity of the muscle and hence complete relaxation, the muscle being in a reversible state of electromechanical sideration. Achieving this state is moreover avoided and not recommended in conventional electro-stimulation. It can only arise thanks to the specific electric parameters of the present invention. It is observed neither in electro-stimulation nor in voluntary contractions.

The device

The entire system allowing electro-inhibition is included in a single device 1.

According to a first preferred embodiment shown in FIG. 1 to 4, it is designed similarly to a spectacle frame that rests on the nose at the front and on the ears at the back by means of two suitable arms. The electronic circuit 3 and the supply 4 in the form of batteries are located in a hollow front part of the device, at the level of flaps 5. The electrodes on the inner and middle faces of the front part 6 are configured so as to be correctly positioned in the area between the eyebrows when the device is placed on a subject.

Figure 2:
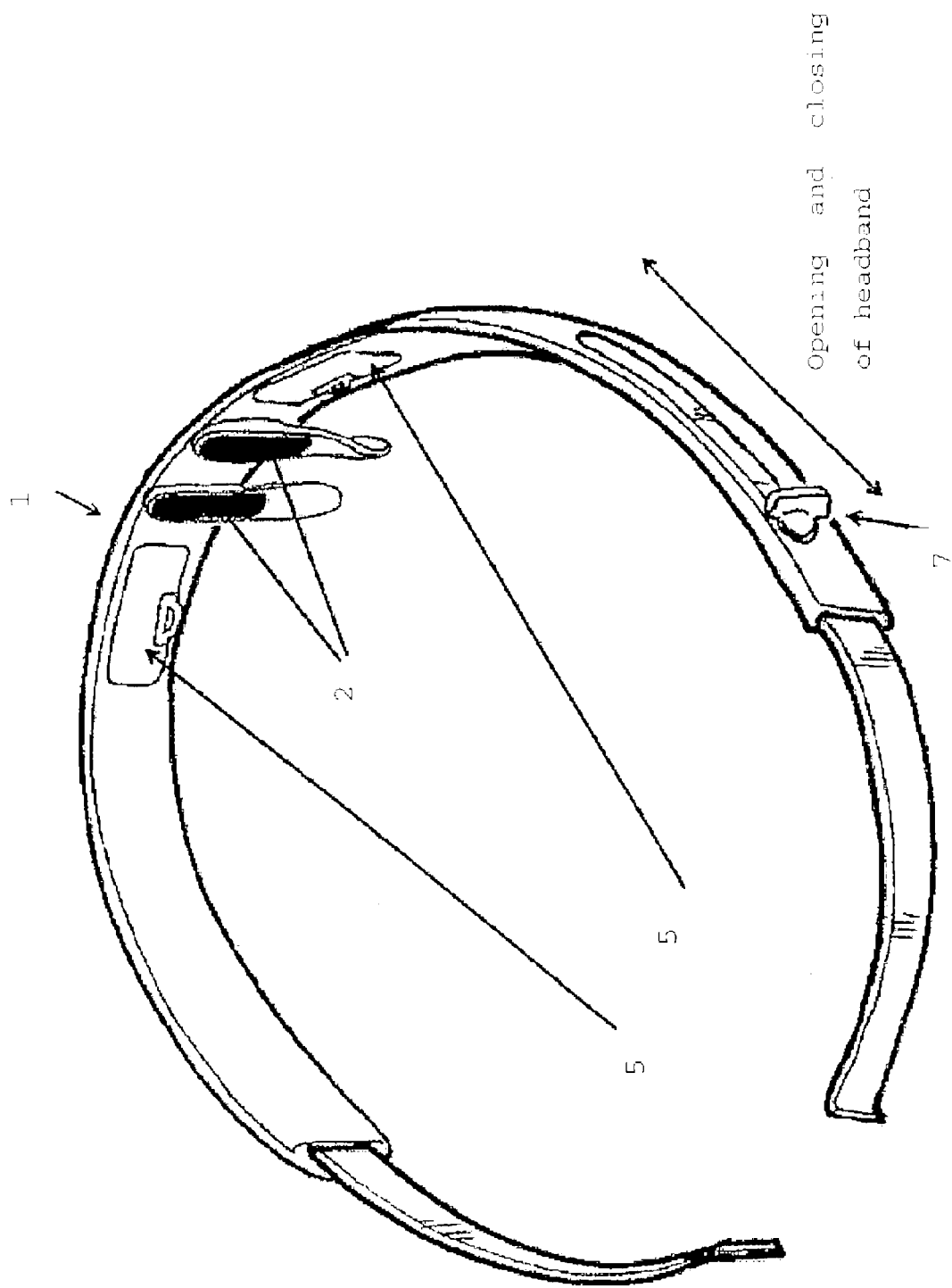
FIG. 2 shows a rear view of the device of FIG. 1.
Figure 3:
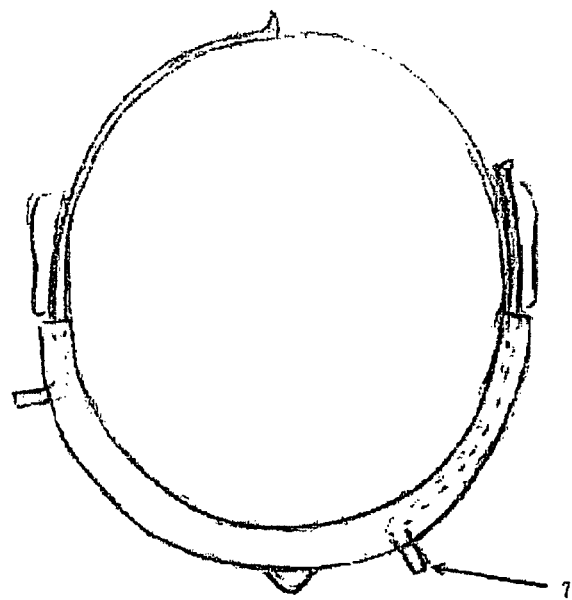
FIG. 3 shows a top view of the device of FIG. 1.
Figure 4:
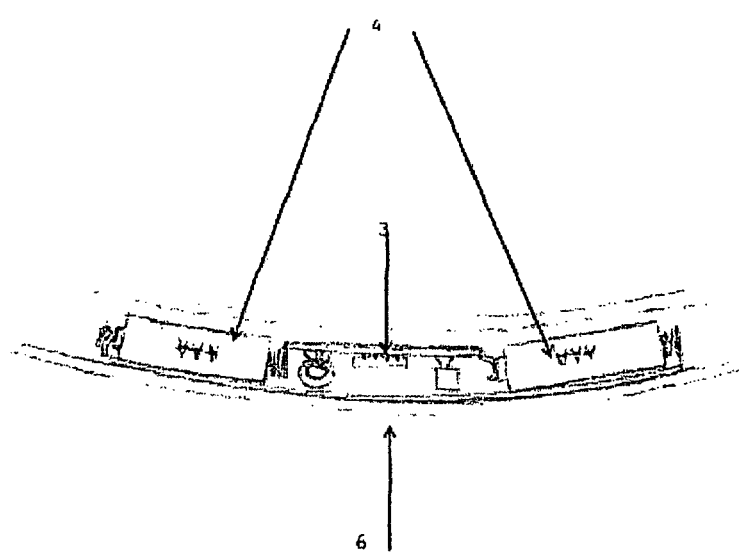
FIG. 4 shows a top cross-section view of the front part of the device of FIG. 1.

Several advantageous embodiments of this device are possible, such as:
  mounting on a headband, as shown in FIG. 2. In this case, an attaching and securing 7 means could be provided which also act as a switch turning on the electricity supply once the headband is in place on the subject,
  mounting on a self-adhesive surface that is placed at the level of the glabella,
  a support hoop of the device resting on the medial line of the skull,
  a little helmet, etc.

According to a second preferred embodiment shown in FIG. 5 to 7, a "double electrode" 2A has been designed, i.e. an electrode in which both conductive poles 2 are borne on a single and same structure. For the user, this arrangement has the convenience of only having to place one single electrode rather than two, as is usually the case in all the traditional techniques of electrotherapy.

The electrode 2A has a shape and size adapted to the area to be treated, i.e. allowing to cover the area of the glabella and to inhibit the pyramidal muscle. According to the invention, the electrode 2A comprises an essentially rectangular piece of cloth 21, the longer side must be positioned more or less vertically, which may have its corners cut at its lower part, placed on the top of the nose, and a rounded upper edge, placed on the forehead (FIG. 7).

The piece of cloth 21 that forms the mechanical support of the electrode is impregnated with two conductive silvered areas 2 that go right through the thickness of the cloth. Thus, the cloth becomes a conductor between its inner surface, placed against the skin, and its outer surface, placed on the side of the contact pads at the level of the electric device. In the state of the art, conduction between the electric device and the electrodes is usually ensured by a cable or a metal snap, the outer surface of the electrode being moreover non-conductive. According to the invention, the outer surfaces of the poles of the electrode are conductive, which allows two conductive pads 25 of the device to come into direct contact with the poles.

Optimum conduction between the conductive areas 2 and the user's skin is ensured by two areas of self-adhesive conductive gel 22 covering said conductive areas on the inner surface of the electrode in contact with the skin. These two conductive gel areas will preferably extend over the whole length of the piece of cloth and, from the outer side edge, over a sufficient width to completely cover the corresponding silvered area 2 (FIG. 7).

An advantageous alternative to impregnation with silver consists in making two holes in the cloth of the electrode to allow the above-mentioned pads to come into direct contact with the conductive gel or with a film of carbon, possibly of carbon covered with a silvered layer, placed between the cloth and the conductive gel (not shown).

The insulation between both poles 2 of the electrode 2A is ensured by a central area 23 devoid of any self-adhesive conductive gel 22.

Still according to an advantageous embodiment of the invention, the electrode 2A is provided with a non-conductive part in the shape of a pin 24 to ensure the mechanical attachment of the support device and of the electrode 2A and to allow both contact pads 25 to precisely fit over both conductive outer areas of the electrode.

As described above, the electronic circuit is located in the central area of the support device 1. From this circuit protrude both contact bands or pads 25 intended to fit over both conductive outer surfaces of the above-mentioned electrode 2A, i.e. both areas of the electrode impregnated with conductive silver.

Between both contact pads 25, the central part of the housing is hollowed and provided with a recess 26 for the pin 24 of the electrode to fit into. This recess 26 is wide at its bottom and narrow at its top, which allows the user to fit the support device with the electrode very easily. As an advantage, the pin 24 comprises a short stem ending in a bulging round head that allows it to be secured in the narrow part of the recess 26 of the support device 1 (FIG. 6).

According to a concrete example, the dimensions of the cloth support 21 are 37 mm×22 mm, the electrodes' dimensions are 21 mm×7 mm, the central area 23 between the electrodes without self-adhesive gel is 5 mm wide and the pin 24 is fixed at a distance of 16.5 mm from the lower edge of the part 2A.

The stability of the support device 1 in the shape of a spectacle frame is provided by three points, for one thing both arms that rest on the ears and for another the electrode stuck to the glabella. This differs from a traditional spectacle frame whose third point of stability is provided by the bridge of the nose or by the plates that rest on the nose. This latter system does not suit the device of the invention since the variations from one person to the other in terms of the size and shape of the nose do not always allow the contact pads to be precisely positioned on the conductive surfaces of the electrode.

Advantages

Apart from the advantages of simplicity and comfort already mentioned above, the device of the invention also has the advantage of being cheap to produce, easy and very quick (typically less than 5 minutes) to use, especially in the user's home, and of not entailing the side effects that are found with injection techniques (allergy, red spots, oedemas, presence of an artificial implant, etc.).

BIBLIOGRAPHICAL REFERENCES

[1] J. P. REILLY, *Impedance and current distribution*, Applied Bioelectricity, $2^{nd}$ Ed., Hardback, Springer-Verlag, N.Y., 1998, pp. 12-45.

[2] L. A. GEDDES and L. E. BAKER, *Electrodes*, Principles of Applied Biomedical Instrumentation, $3^{rd}$ Ed., John Wiley & Sons, 1989, pp. 315-387.

[3] L. A. GEDDES and L. E. BAKER, *Stimulators and Stimulation*, Principles of Applied Biomedical Instrumentation, 3rd Ed., John Wiley & Sons, 1989, pp. 453-469.

[4] D. A. JONES and B. BIGLAND-RITCHIE, *Excitation Frequency and Muscle Fatigue: Mechanical Responses during Voluntary and Stimulated Contractions*, Experimental Neurology 64, pp. 401-413 (1979).

[5] D. A. JONES, *Muscle Fatigue due to Changes beyond the Neuromuscular Junction*, Human Muscle Fatigue: Physiological Mechanisms, Pitman Medical London, 1981 (Ciba Foundation Symposium 82), pp. 178-196.

[6] B. BIGLAND-RITCHIE, *EMG and Fatigue of Human Voluntary and Stimulated Contractions*, Human Muscle Fatigue: Physiological Mechanisms, Pitman Medical London 1981 (Ciba Foundation symposium 82), pp. 130-156.

[7] D. A. JONES, *High and Low-Frequency Fatigue Revisited*, Acta Physiol. Scand. 156, 265-270 (1996).

[8] A. C. GUYTON, *Reciprocal Innervation*, Textbook of Medical Physiology, 5th Edition, Sanders Company, 1976, pp. 626-27.

[9] J. B. WAL, *Modulation of Spasticity: Prolonged Suppression of a Spadal Reflex by Electric Stimulation*, Science 216: 203-204, 1982.

[10] M. G. LEVIN, M. KNOTT and H. KABAT, *Relaxation of Spasticity by Electric Stimulation of Antagonist Muscles*, Arch. Phys. Med. 33: 668-673, 1952.

[11] A. C. GUYTON, *Tendon Reflex*, Textbook of Medical Physiology, 5th edition, Sanders Company, 1976, pp. 623-24.

[12] J. HOUK and E. HENNEMAN, *Responses of Golgi tendon organs to active contractions of the soleus muscle of the cat*, J. Neurophysiol. 30: 466, 1967.

The invention claimed is:

1. A Stand-Alone Device for the electro-inhibition of facial muscles comprising:
a user's head support is configured to be at the level of a user's head similar to a spectacle frame with two arms configured to rest on the ears of a user,
a removable single electrode structure comprising two contact electrodes configured to be positioned on either sides of the upper part of the nose of the user at the level of the glabella, said single electrode structure also comprising a piece of cloth acting as a support for said contact electrodes, the contact electrodes being covered on their inner face by a self-adhesive conductive gel, the inner face being a face that is in contact with the user's skin, said single electrode structure being removable from the user's head support,
an electronic circuit having pads, the electronic circuit being integrated in the user's head support for generating low-voltage electric impulses in said contact electrodes when brought into contact with said pads of the electronic circuit and a direct-current electricity supply integrated in the user's head support,
wherein both contact electrodes are in the shape of two conductive silvered areas that impregnate said cloth, the cloth being conductive on both its inner and outer faces, wherein the faces are in contact with said pads of the electronic circuit; and
wherein the single electrode structure is provided with a non-conductive part in the shape of a pin to ensure the mechanical attachment of said single electrodes structure into a recess of the user's head support with said pads of the electronic circuit being brought into contact with the respective contact electrodes.

2. Device as in claim 1, wherein two holes are made in the piece of cloth to allow said pads to come into direct contact with said self-adhesive conductive gel or with a carbon film, covered with a layer of silver inserted between the cloth and the conductive gel.

3. Device as in claim 1, wherein the conductive gel is applied in the form of areas extending over the whole length of the piece of cloth and extending, from the outer lateral edge, over a width that is sufficient to completely cover both contact electrodes.

4. Device as in claim 3, wherein the piece of cloth has a central area devoid of any conductive gel in order to ensure the electric insulation between the contact electrodes.

5. Device as in claim 1, wherein the single structure made of cloth has an essentially rectangular shape with the long side or length of the rectangle arranged more or less vertically and on which the contact electrodes are separated from each other by a distance between 3 and 15 mm.

6. Device as in claim 1, wherein the pin comprises a short stem topped by a bulging round head which can fit into the narrow part of a recess of user's head support which is wider at its bottom than at its top.

7. Device as in claim 1, wherein the user's head support is in the form of a headband configured to be positioned on the forehead.

8. Device as in claim 7, wherein the headband comprises securing means configured to be in locked and unlocked position respectively, so that the system acts both as a closed and open switch respectively.

9. Device as in claim 1, wherein the user's head support is in the form of supporting a hoop configured to rest on the medial line of the skull.

10. Device as in claim 1, wherein the user's head support is in the form of a helmet made of light material.

11. The Device as in claim 1, wherein the user's head support, the integrated electrical circuit and the integrated electricity supply are free of an external power source.

12. The Device as in claim 1, wherein the user's head support, the integrated electrical circuit and the integrated electricity supply are free of an external electronic circuit for generating low voltage electric pulses in the contact electrodes.

13. The Device as in claim 1, wherein two arms of the spectacle frame provide a first and a second point of stability contacting a user and the mechanical attachment to the removable single electrode structure provides a third point of stability contacting the user.

14. A Device for the electro-inhibition of facial muscles comprising:
a user's head support device configured to be at the level of a user's head having a frame with two arms configured for resting on the ears of the user, a single electrode structure including:
- two contact electrodes configured to be positioned on either side of the upper part of the nose at the level of the glabella,
- a piece of cloth acting as a support for said contact electrodes, the contact electrodes being covered on their inner face by a self-adhesive conductive gel, the inner face being a face that is in contact with the user's skin, said single electrode structure being removable from the user's head support device;
- both contact electrodes are in the shape of two conductive silvered areas that impregnate said cloth, the cloth being conductive on both its inner and outer faces, wherein the faces are in contact with pads of the electronic circuit;

an electronic circuit having pads in contact with the faces of the contact electrodes, the electronic circuit integrated in the user's head support device for generating low-voltage electric impulses in said contact electrodes when brought into contact with said pads of the electronic circuit and a direct-current electricity supply integrated in the user's head support device;

the single electrode structure having a non-conductive part in the shape of a pin to ensure the mechanical attachment of said single electrodes structure into a recess of the user's head support device with said pads of the electronic circuit being brought into contact with the respective contact electrodes; and wherein the device has only three points of stability configured for contacting the user, the two arms of the frame provide a first and a second point of stability configured for contacting the user and the single electrode structure configured for being attached to the user's skin at the glabella provides a third point of stability contacting the user.

15. The Device as in claim 14, wherein the user's head support device is configured so as a support thereof at the level of the user's head is not provided by the nose of the user.

16. The Device as in claim 14, wherein the user's head support device, the integrated electrical circuit and the integrated electricity supply comprise a stand-alone device free of an external electricity supply.

* * * * *

UNITED STATES PATENT AND TRADEMARK OFFICE
CERTIFICATE OF CORRECTION

| | | |
|---|---|---|
| PATENT NO. | : 8,914,123 B2 | Page 1 of 1 |
| APPLICATION NO. | : 11/667223 | |
| DATED | : December 16, 2014 | |
| INVENTOR(S) | : Pierre Rigaux | |

It is certified that error appears in the above-identified patent and that said Letters Patent is hereby corrected as shown below:

In the Claims
Column 8, line 46, claim 9, delete "supporting a hoop" insert --a supporting hoop--

Signed and Sealed this
Nineteenth Day of May, 2015

Michelle K. Lee
*Director of the United States Patent and Trademark Office*